United States Patent
Maschke

(10) Patent No.: US 7,835,496 B2
(45) Date of Patent: Nov. 16, 2010

(54) USER INTERFACE OF AN X-RAY SYSTEM AND METHOD FOR MANUFACTURING SUCH AN USER INTERFACE

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 176 days.

(21) Appl. No.: 12/107,097

(22) Filed: Apr. 22, 2008

(65) Prior Publication Data

US 2009/0262896 A1  Oct. 22, 2009

(51) Int. Cl.
*H05G 1/08* (2006.01)

(52) U.S. Cl. .......................... 378/91; 378/62

(58) Field of Classification Search ............ 378/62, 378/91, 98.7
See application file for complete search history.

(56) References Cited

U.S. PATENT DOCUMENTS

| | | | |
|---|---|---|---|
| 4,160,906 A * | 7/1979 | Daniels et al. ............... 378/97 |
| 4,504,858 A | 3/1985 | Franke | |
| 4,597,094 A * | 6/1986 | Kleinman .................... 378/95 |
| 4,773,086 A * | 9/1988 | Fujita et al. ..................... 378/4 |
| 5,231,651 A * | 7/1993 | Ozaki et al. ..................... 378/4 |
| 5,349,625 A * | 9/1994 | Born et al. .................... 378/95 |
| 5,737,386 A * | 4/1998 | Strawder ...................... 378/95 |
| 5,949,811 A * | 9/1999 | Baba et al. .................. 378/108 |
| 5,963,613 A | 10/1999 | Navab | |
| 6,178,228 B1 * | 1/2001 | Schol .......................... 378/162 |
| 6,233,310 B1 * | 5/2001 | Relihan et al. .............. 378/108 |
| 6,259,767 B1 * | 7/2001 | Neumann et al. ........... 378/151 |
| 6,292,537 B1 * | 9/2001 | Zimmermann .............. 378/108 |
| 6,512,808 B2 * | 1/2003 | Klingenbeck-Regn ....... 378/18 |
| 6,647,283 B2 * | 11/2003 | Klotz .......................... 600/425 |
| 6,850,597 B2 * | 2/2005 | Matsumoto et al. ......... 378/154 |
| 6,859,513 B2 * | 2/2005 | Sako ............................ 378/16 |
| 6,920,201 B2 * | 7/2005 | Maack et al. ............... 378/116 |
| 6,934,356 B1 * | 8/2005 | Satheesan et al. ............. 378/62 |
| 7,103,134 B2 * | 9/2006 | Suzuki ........................... 378/4 |
| 7,120,229 B2 * | 10/2006 | Takasawa .................. 378/98.2 |
| 7,178,980 B2 * | 2/2007 | Groh et al. .................. 378/207 |
| 7,542,792 B2 * | 6/2009 | Wollenweber et al. ....... 600/407 |
| 7,587,023 B2 * | 9/2009 | Hur .............................. 378/16 |
| 7,620,152 B2 * | 11/2009 | Yoshida ...................... 378/108 |
| 7,623,622 B2 * | 11/2009 | Camus et al. ................. 378/62 |
| 7,634,308 B2 * | 12/2009 | Ogawa ........................ 600/431 |
| 7,715,522 B2 * | 5/2010 | Goto et al. .................... 378/16 |
| 7,734,006 B2 * | 6/2010 | Miyazaki et al. ............... 378/8 |
| 2006/0120507 A1 | 6/2006 | Brunner et al. | |

FOREIGN PATENT DOCUMENTS

DE    102005016472 A1    10/2006

* cited by examiner

Primary Examiner—Allen C. Ho

(57) ABSTRACT

The invention relates to an user interface comprising: a read only memory for an operating parameter of an X-ray system with each one section for contrast medium injection, for data acquisition, for reconstruction of data, for image storage and for displaying of an image; a write-read-memory for the operating parameter which has to be transferred to the corresponding section of the X-ray system; and a control unit for copying the operating parameter from the read only memory into the write-read-memory. The copied operating parameter is graphically supported within the write-read-memory alterable.

8 Claims, 3 Drawing Sheets

USER INTERFACE OF AN X-RAY SYSTEM AND METHOD FOR MANUFACTURING SUCH AN USER INTERFACE

FIELD OF THE INVENTION

This invention relates to an user interface of an X-ray system. Furthermore this invention relates to a method for manufacturing such an user interface.

BACKGROUND OF THE INVENTION

Imaging devices are used to support a diagnosis and therapies of many medical diseases. New imaging techniques like Computed Tomography (CT) and Magnetic Resonance Imaging (MRI) are becoming more and more popular. X-ray technology and devices which have been known in their basic principles since 1890, are still being used because they provide medical images very fast and with high resolution. The disadvantage of these traditional X-ray systems is the lack of digital and/or 3D image capabilities.

Approximately in 1980 the first digital angiographic X-ray imaging systems came into use. Such an X-ray system is disclosed in U.S. Pat. No. 4,504,858 "X-Ray Diagnostic System for Angiographic X-Ray Examination". One of the first commercial products was the Digitron from Siemens in 1983.

Approximately since 1995 the first angiographic X-ray imaging system has been in use which allows 3D imaging of static objects, in particular of humans organs. Parts of such an X-ray system are disclosed in U.S. Pat. No. 5,963,613 "C-arm Calibration Method for 3 D Reconstruction in an Imaging System". These systems use an X-ray source and an X-ray detector mounted on a C-arm which rotates within a predetermined angle (usually around 220 degrees) around the patient to collect a number of two-dimensional X-ray projections. Before acquiring this data, a contrast agent is injected into a vessel of an organ which will be examined, for example the vessels of the brain. The two-dimensional X-ray projections are transferred to a special processor, usually an additional computer workstation, for reconstruction of a 3D volume image.

In the 1990s the X-ray detectors were image intensifiers, which since the beginning of the century have been more and more replaced by flat-panel X-ray detectors, usually based on amorphous silicon (aSi). The benefit of the flat-panel detectors are larger image size, a better access to the patient and a better image quality. Although the lower weight of the flat-panel detector allows faster rotating speed of the C-arm, these possibilities have not been really used. A typical product which allows 3D high contrast imaging is the AXIOM Artis dTA, with the syngo InSpace 3D Workstation from Siemens.

In 2006 the first C-arm X-ray system which provided CT-like imaging, particular low contrast imaging, was introduced to the medical market by the Siemens AG and called DynaCT. This solution is disclosed in US2006/0120507, "Angiographic X-ray Diagnostic Device for Relational Angiography". This document, however, does not disclose any clinical protocols and procedures. A clinical protocol and/or a procedure comprises any medical method and/or means including a method for anamnesis, diagnostics, prophylaxis, treatment and monitoring of a patient.

DE 10 2005 016 472 A1 "Betriebsverfahren für eine Röntgenanlage, korrespondierendes Betriebsverfahren für einen Rechner und entsprechende Gegenstände" discloses an X-ray system which allows through a particular synchronization with the ECG of the patient, that CT-like imaging of the heart particular low contrast imaging can be reconstructed.

These above mentioned X-ray systems are having an user interface and several control elements to select technical parameters of the system. The drawback is that the user needs to have a technical understanding of the system to operate it properly. In most cases the user even needs to set on different subsystems and components specific parameters e.g. the voltage and current on a generator control, the parameters for 3D high-contrast imaging on an imaging subsystem, the parameters for 3D low contrast imaging on a separate computer workstation and a parameter for a injection protocol on a contrast media injector.

This situation today is close to the first cars, if the driver wanted a specific performance, e.g. during cold and moist weather, he had to reduce the gap of the electrodes in the spark plug and change additionally the ignition timing during the driving.

SUMMARY OF THE INVENTION

It is one object of the invention to provide an X-ray system which is easy to use. This object is achieved by a user interface of an X-ray system with storage means, comprising:
a) a read-only memory for at least one operating parameter of said X-ray system with each one section for contrast medium injection, for data acquisition, for reconstruction of said data, for image storage and for displaying of said image,
b) a write-read-memory for said operating parameter, which has to be transferred to the corresponding section of said X-ray system, and
c) a control unit for copying said operating parameter from said read only memory into said write-read-memory and said copied operating parameter is graphically supported alterable.

The user can choose a predefined clinical procedure from the user interface and the operating parameter of all sections and components of the X-ray system are set by a data set stored in the read only memory. This data set is part of a data base and set s up the X-ray system optimally for e.g. a clinical exploration. The user interface of this invention designs the X-ray system for a predefined therapy i.e, the optimal operating parameters are copied into the write-read-memory and are transferred to the sections of the X-ray system, so as to facilitate a safe adjustment of the X-ray system for a selected procedure.

The operating parameters for each clinical procedure are preferably factory-made in the read only memory by the manufacturer, based on experiences. Thus a factory-built data base of various sets of the operating parameters is provided by the read only memory.

It is another object of this invention, that the user has not a heavy workload by setting up that complex X-ray system. The user could take his focus on the interpretation of the infomation acquired by the X-ray system. That shortens time needed for an examination or a therapy of a patient and thus lowers the costs.

The predefined operating parameter is preferably editable by the user interface. The copied operating parameter is editable in the write-read-memory. Preferably, a "Default"-function of the user interface resets the operating parameter. The operation parameter of the read only memory for example is again copied into the write-read-memory for setting the factory settings.

It is irrelevant for this invention, if the operation parameter is administered by a central system control unit, by several sections of the X-ray system each or an image building workstation. The operating parameter is transferred from the user interface to the corresponding component via an internal data bus or an internal network. Each of the components of the X-ray system processes only their parameter.

If a user has at one point of the started clinical procedure to accomplish an action, the user interface preferably gives a graphical and/or an acoustic indication. This feature of the user interface can be edited and/or can be switched off by the user. To achieve this, merely the operating parameter copied to the write-read-memory has to be altered.

In addition to these user indications, the user interface is connectable with a loudspeaker and/or headphone to give a directive to the patient. The directive for the patient could be "Inhale, stop breathing, breath out" for instance. This function of the user interface again can be edited and/or can be switched off.

The user interface has a button for changeover to the conventional manual control of the X-ray system. This button is labelled for example with "manual".

The operating parameters may comprise among others: For the data acquisition section: A tube voltage in kV, including tube voltages of about 30 kV to about 150 kV for an X-ray source. The voltage is graphically indicated and alterable with a scroll bar. The operating parameter defines an X-ray focus by its size and shape, which is graphically indicated by an outline or an icon for example and could be selected by pushing or clicking the button. Another operating parameter is a system dose in μGray per frame which includes a range of about 0.1 to 2.5 μGee. The operating parameter defines a so called scan time and/or also an acquisition time for any projection or all the projections of one slide in seconds. An increment in angular dimensions, such as angular degrees, may define a distance between two acquisitions by an angiographic X-ray system as the operation parameter. A number of projections may also be transferred to a C-arm as an operation parameter and describes a number of acquisitions per slice. One operating parameter is a gating to define whether an acquisition is conducted with or without triggering, for example with an ECG and/or a respiration signal. A further operation parameter may be the number of runs, wherein a "run" is one sweep of the C-arm, during which 2D projection images are acquired. One run may comprise a rotation within an angle range of around 180° to 360°, usually around 200°-220° degrees, and the acquisition of around 150 to 300 projection images.

Another possible operation parameter for the reconstruction section of the X-ray system is a modus for calculation of a first reconstruction. A so called volume of interest VOI—is an operation parameter which cuts off a part of the reconstruction and is to be calculated from the two-dimensional X-ray projections. Another preferred operating parameter is a so called slice matrix referring to the size of the slice, as for example a slice matrix of 256×256 pixels or voxels. Another possible operating parameter defines different kernels. A kernel is part of an algorithm which reduces noise in the image and smoothes the image impression. Further operating parameters can predetermine an image characteristic. These operating parameters could even be set up for a primary and for a secondary image reconstruction. Usually, the sections of the X-ray system for image reconstruction are identical. However the operating parameters for these two sections may be unequal or equal.

Further operating parameters stored in the read-only memory of the user interface may relate to a viewing modus, an image post-processing or a combination thereof. A predefined image layout or image partition may define how the reconstructed images are displayed on a set of monitors arranged like a rack of several monitors, or on a large-scale display or a video projector. A 2D-, 3D- or 4D-representation as another operating parameter may define a type of visualization and the scope of the information to be displayed. A specific method of image reconstruction may be defined by an operating parameter from a set of volume rendering technologies. One example value of the operating parameter is an MPR (Multiplanar Reformation) viewing modus, in which multiple slices are generated from a 3D volume. In particular, three slices through the 3D volume are displayed, wherein all three slices are perpendicular to each other. A so called maximum intensity projection could also be selected by the operating parameter. With a thickness of layers is defined how many slices of projections are employed for the representation. A further operating parameter by be a windowing parameter, in particular the centre and width of a window. Windowing is the process of selecting some segment of the range of pixel values which can be found in any one image (for examples between 0 and 255) by the definition of a window centre and a window width and then displaying the pixel values within that segment (e.g. all pixel values between 50 and 150) over the full brightness range from white to black. Thus, contrast will be visible only for the pixel values within the selected window. A predefined centre and width can be used for certain images of the same type. With an operating parameter for an adjustable contrast or brightness a cut of the image is to be accented. A further set of operating parameters may be a Look-Up Table (LUT), which are used to provide a non-linear correlation between a pixel value and the gray scale value which is displayed.

Additional operating parameters are provided for the injector of contrast medium. This includes a measure of quantity of the contrast medium in ccm, a portion of contrast medium in percentage or a portion of saline solution, respectively. An administration rate for the contrast medium in ccm per second is also to be stored in the read-only memory as a duration of injection in seconds as operating parameter. A delay of the data acquisition in seconds constitutes a time lag between start or end of administration of contrast medium and the acquisition of projections. One operating parameter indicates a catheter size in French or a place for injection. Furthermore, another operating parameter may determine a concentration of contrast medium in mg per ml or specify the contrast medium as for example iodine for a predetermined procedure.

Possible operating parameters for the image storage comprise points for a data reduction factor for archiving as a matrix size of the images to be stored. The operating parameter defines another data reduction factor for an image layout which is also another matrix size of the images to be stored. Another operating parameter defines a target address for image layout and/or archiving.

It is another object of this invention to provide a method for manufacturing an user interface described in detail above.

BRIEF DESCRIPTION OF THE DRAWINGS

Some preferred embodiments of the invention are described with reference to the accomplished drawings.

The drawings showing

DETAILED DESCRIPTION OF THE INVENTION

Figure 1:
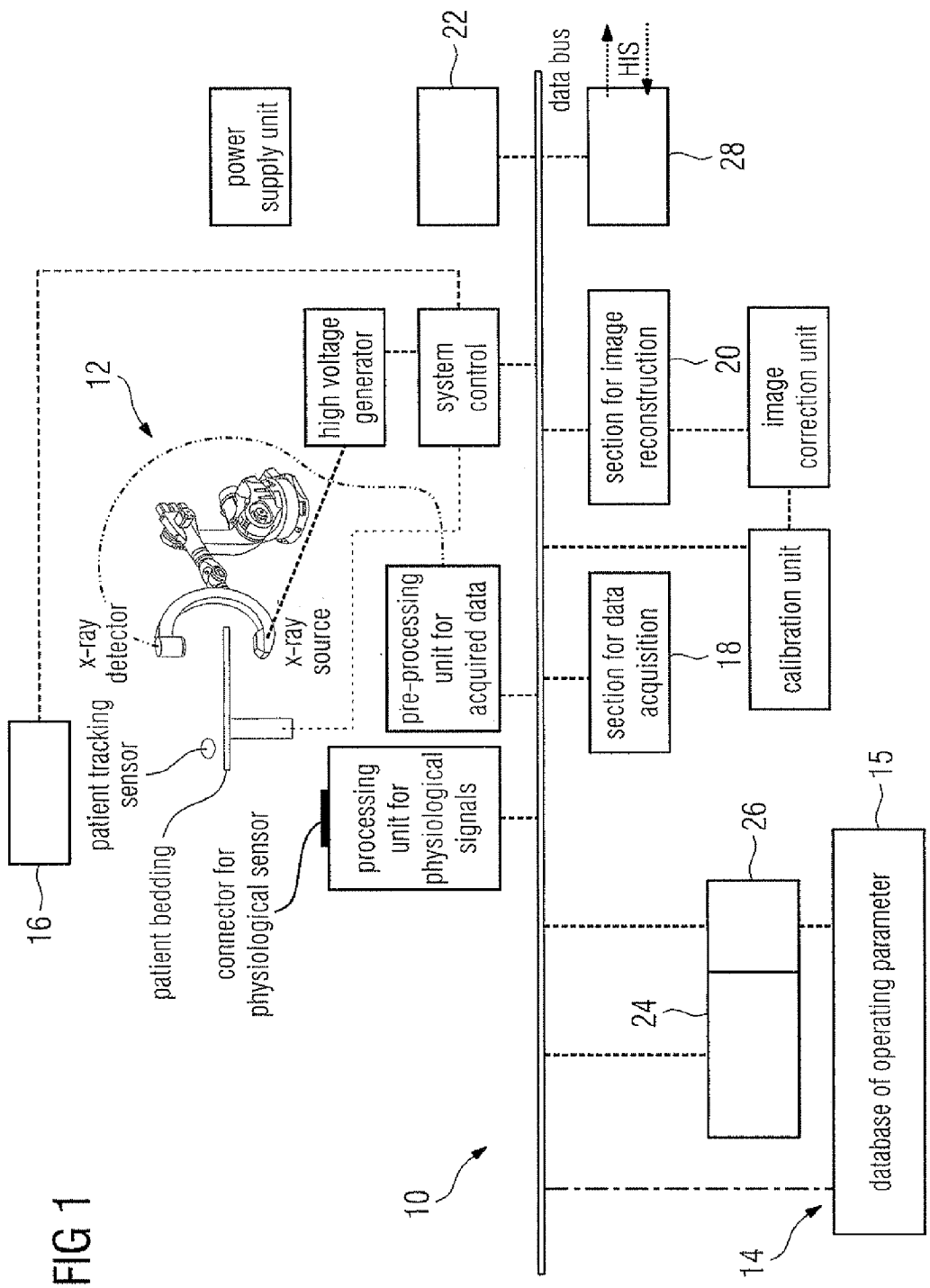
FIG. 1 a first embodiment of an user interface connected with an X-ray system.

FIG. 1 shows an X-ray system 12 with a power supply unit connected with a high voltage generator supplying an X-ray source as an X-ray tube or alike. The X-ray source is mounted on a C-arm of an angiographic X-ray system which bears an X-ray detector on the other side of the C-arm and in-between a patient bedding. This section is guided by a system control which is also connected with a section for contrast medium injection 16. The system control unit of the X-ray section is connected with a data bus of an user interface 10 with storage means 14, comprising a read only memory for at least one operating parameter 15 of a section above mentioned or for a another section shown in FIG. 1, especially for data acquisition 18, for reconstruction 20 of acquired data, for image storage 22 and for displaying 24 of the image. All these sections 12, 14, 16, 18, 20 and 22 are interconnected for data transfer by a data bus.

The storage means 14 comprising also a write-read-memory for the operating parameter 15 which has to be transferred to the corresponding sections of the X-ray system 12 by the data bus. The operating parameter 15 is copied from the read only memory into the write-read-memory via a control unit 26 of the user interface 10 and the copied operating parameter 15 within said write-read-memory is graphically supported alterable. Thus the section 24 for displaying images is providing a video device for visualization of the operating parameter 15.

Figure 2:
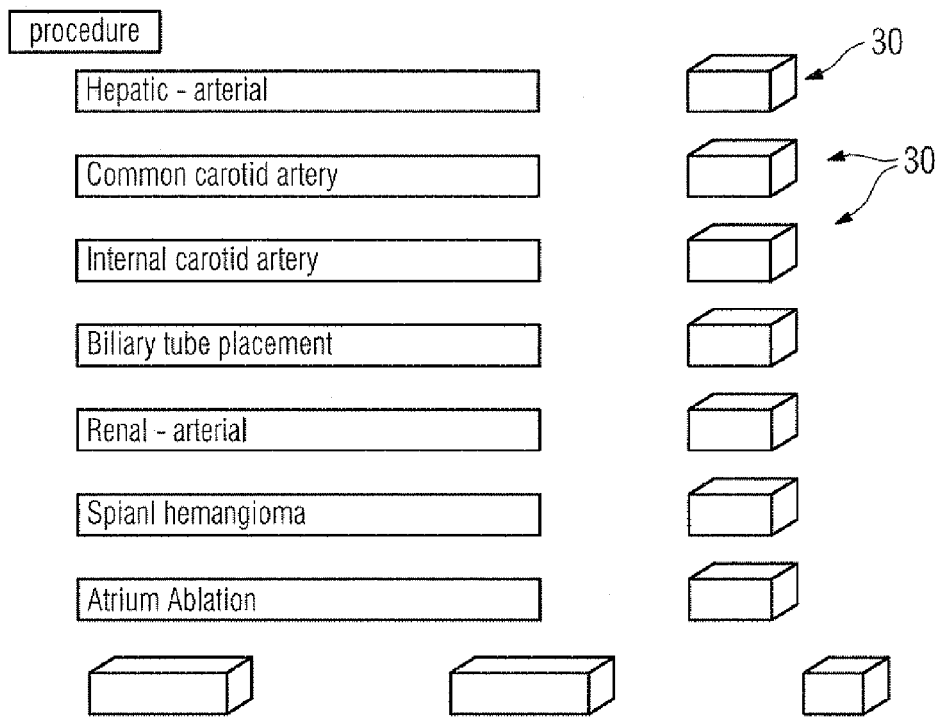
FIG. 2 a graphical visualization of operating parameters which are alterable according to the embodiment illustrated in FIG. 1.

A first embodiment of the visualization is shown in FIG. 2. The storage means 14 provide several sets of operating parameter 15 for some procedures which are factory set. By pushing a button 30 viewed in the same row the medical procedures is selected.

Such a procedure is a workflow like the following:

First step is to pick up a patient and archiving 28 his data. On the screen of the displaying section 24 some procedures are listed and one of them is selected by pushing the button 30. For example by pushing a button 30 the procedure "Hepatic-arterial" is selected. The control unit 26 copies the operating parameter 15 from the read only memory to the write-read-memory which causes the system to give an indication for optimal positioning of the patient on the patient bedding as shown in FIG. 1. Therefore an operating parameter 15 for positioning the patient in an isocentric point of the C-arm is transferred to the system control of the X-ray system 12.

Figure 3:
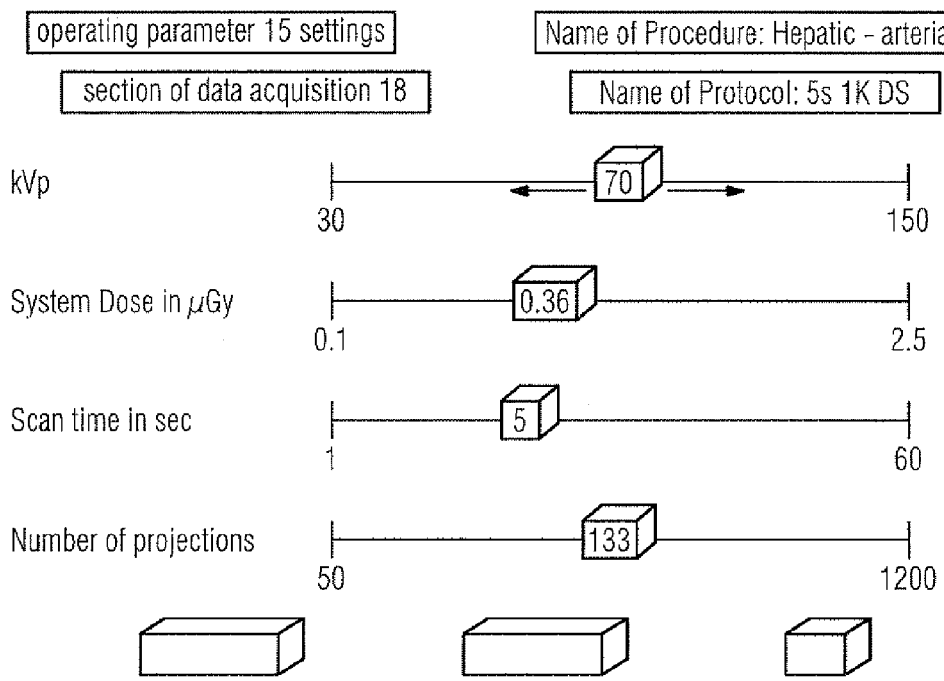
FIG. 3 a graphical visualization of fisher operating parameters which are alterable with an user interface shown in FIG. 1.

After the optimal position is adopted the system starts the procedure. A second embodiment of the visualization of operating parameters 15 is displayed like in FIG. 3 illustrated. This operating parameters 15 are predefined by values stored in the read only memory of the storage means 14 of the user interface 10. However beside the actual settings of the operating parameter 15 a lower limit and upper limit is graphically indicated with a scrollbar. The upper row shows for example a scrollbar for changing the tube voltage in kV which could be changed in the range of about 30 kV to about 150 kV. The graphical support comprises also an indication of the setting as a number "70" at the scroll box. Another operating parameters 15 comprises the system dose in μGray per frame, a scan time in seconds and a number of projections to be made for each slice. These actual settings are also indicated by the scroll boxes respectively. The operating parameters 15 are short indicated by a protocol name like "5s 1K DS".

If these settings are made the system gives a next indication: "Attention approaching start position". These indications are transferred by a headset or a loudspeaker to the patient. Then the X-ray system 12 approaches the start position. Another system indication as "Attention a test run at low speed will be carried out" will follow. After the test ran is completed a new indication will appear: "Attention an X-raying will be carried out" which samples water values for further image corrections.

All operating parameters 15 of each section of the X-ray system 12 e.g. for data acquisition 18 a tube voltage, a tube focus, a system radiation dose, an acquisition duration, an angle step size/increment, a number of projections and/or a triggering are transmitted via data bus from the write-read-memory 14 of the user interface 10. The data acquisition section 18 is set up with these operating parameters 15. Thus neither adjustment for the complex system is ignored nor any adjustment conflicts with other adjustments because the user interface 10 dumps an error message.

Figure 4:
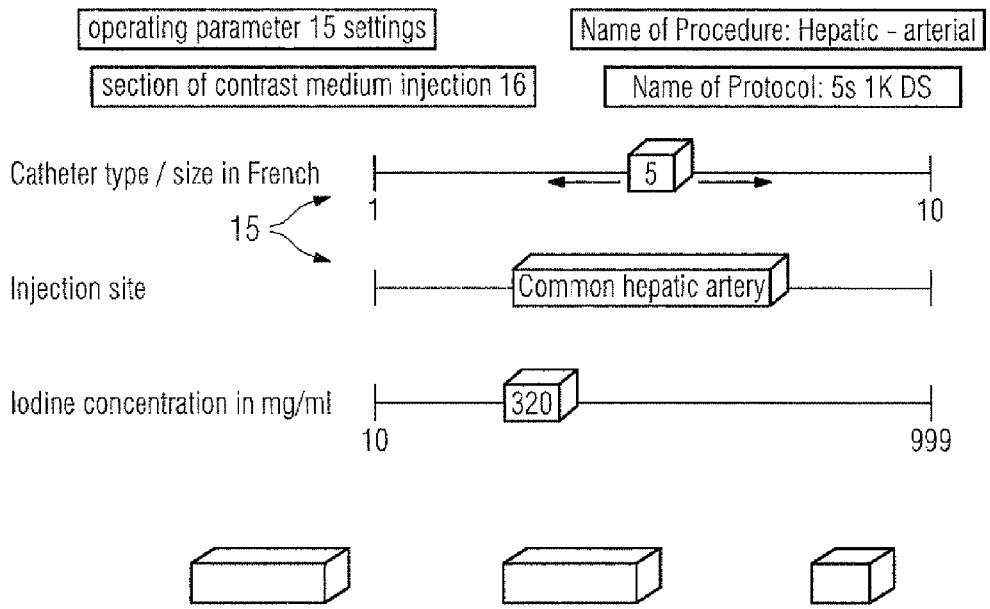
FIG. 4 a graphical visualization of further operating parameters which are alterable with an user interface shown in FIG. 1.
Figure 5:
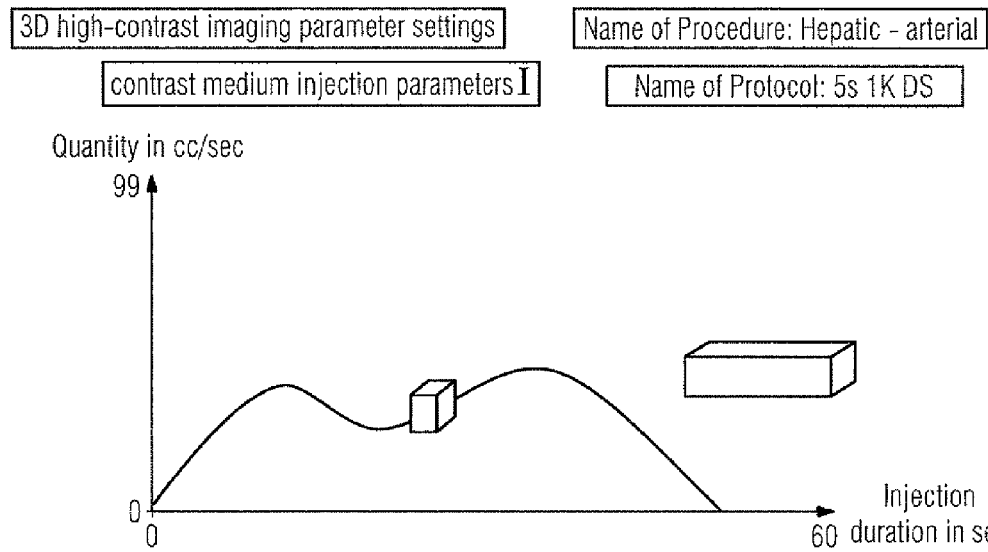
FIG. 5 a graphical visualization of an operating parameter which is graphically supported alterable with an user interface shown in FIG. 1.

Again another visualization shown in FIG. 4 will appear on the screen of the section for displaying of images 24. This chapter of operating parameters 15 displays the settings for catheter size in French, defines an injection site which is a pull down menu with several sites like "common artery" and defines concentration of contrast medium. A graphical supported change of an operation parameter 15 is shown in FIG. 5. A curve illustrates a quantity of administered contrast medium over an injection time. A cursor is visualized on the curve which is displaced along the curve by moving the cursor. The system prompts again an indication like "Attention contrast medium is injected" and the chosen contrast medium is administered in the predefined rate and quantity by the injector section 16.

An indication like "Attention 3D acquisition will prepared" and an indication to the patient like "Please lie quiet. Breath in, stop breathing" is performed by the user interface 10. A 3D -acquisition with the operation parameter 15 for the acquisition section 18 is set up and thereafter an indication to the patient like "breath out, breath normally please" will follow.

Within a section for image reconstruction 20 shown in FIG. 1 a three-dimensional image is calculated with operating parameter 15 of the user interface 10 which comprises a calculation mode, a VOI, a layer matrix, a kernel and/or an image characteristic.

The calculated images are stored in the image storage section 22 and displayed by the section 24. After viewing by the user an archiving of the images and a layout/display is performed automatically by the user interface 10. However the operating parameter 15 predetermines for example an image resolution, an image layout, a two, three or four dimensional representation, a VRT (Volume Rendering Technique), a MPR, a layer thickness, a window level, an image contrast, an image brightness and/or an LUT (Look-up Table).

After an approval by the user the patient is released. The user interface 10 updates expendable items such as catheters and keep s records of the procedure as digital audio recordings of diagnostic findings and/or handpicked images, for example or possibly additional digital video recordings of the examination room.

The invention claimed is:

1. An user interface of an X-ray system, comprising:
   a read only memory that stores for each of a plurality of predefined clinical procedures corresponding one or more optimal operating parameters for each corresponding section of the X-ray system as default settings, wherein at least one of the optimal operating parameters is selected from the group consisting of: an operating parameter for injecting a contrast medium, an operating parameter for acquiring data, an operating parameter for reconstructing data, an operating parameter for storing an image, and an operating parameter for displaying an image, and wherein at least one of the optimal operating parameters is for injecting the contrast medium and is selected from the group consisting of: a quantity of the contrast medium, a saline solution to be administered, an administration rate, a duration of the injection, a delay up to the data acquisition, a catheter size, a place for the injection, a concentration of the contrast medium, and a type of the contrast medium;

a user interface for displaying a list of the predefined clinical procedures available for selection;

a control unit that receives a selection of one of the predefined clinical procedures from the list and copies the corresponding one or more optimal operating parameters from the read only memory as default settings into a write-read-memory;

wherein the user interface further comprises an edit interface for graphically displaying and receiving changes to the optimal operating parameters from their default settings into a current configuration stored in the write-read-memory for the operating parameters; and wherein the control unit transfers the current configuration for the operating parameters from the write-read-memory to each corresponding section the X-ray system to facilitate adjustment of the X-ray system for the selected clinical procedure.

2. The user interface according to claim 1, wherein at least one of the optimal operating parameters is for acquiring the data and is selected from the group consisting of: a tube voltage, a tube focus, a system radiation dose, an acquisition duration, an angle, a step size, a step increment, a number of projections, a triggering, and a number of runs.

3. The user interface according to claim 1, wherein at least one of the optimal operating parameters is for reconstructing the data and is selected from the group consisting of: a mode, a volume of interest, a layer matrix, a kernel, and an image characteristic.

4. The user interface according to claim 1, wherein at least one of the optimal operating parameters is for displaying the image and is selected from the group consisting of: an image resolution, an image layout, a two dimensional representation, a three dimensional representation, a four dimensional representation, a Volume Rendering Technique, a Multiplanar Reformation, a layer thickness, a window level, an image contrast, an image brightness and an Look-up Table.

5. The user interface according to claim 1, wherein at least one of the optimal operating parameters is for storing the image and is selected from the group consisting of: points for reducing the data for archiving, an image layout, a target address for the image layout, and a target address for the archiving.

6. The user interface of claim 1 wherein the edit interface restricts changes to the optimal operating parameters from their default settings to an upper and a lower limit.

7. A method for configuring operating parameters via an user interface of an X-ray system, comprising:

storing for each of a plurality of predefined clinical procedures in a read only memory corresponding one or more optimal operating parameters for each corresponding section of the X-ray system as default settings, wherein at least one of the optimal operating parameters is selected from the group consisting of: an operating parameter for injecting a contrast medium, an operating parameter for acquiring data, an operating parameter for reconstructing data, an operating parameter for storing an image, and an operating parameter for displaying an image, and wherein at least one of the optimal operating parameters is for injecting the contrast medium and is selected from the group consisting of: a quantity of the contrast medium, a saline solution to be administered, an administration rate, a duration of the injection, a delay up to the data acquisition, a catheter size, a place for the injection, a concentration of the contrast medium, and a type of the contrast medium;

displaying a list of the predefined clinical procedures available for selection via the user interface;

receiving a selection of one of the predefined clinical procedures from the list and copying the corresponding one or more optimal operating parameters from the read only memory as default settings into a write-read-memory;

graphically displaying and receiving via the user interface changes to the optimal operating parameters from their default settings into a current configuration for the operating parameters stored in the write-read-memory; and transferring the current configuration for the operating parameters from the write-read-memory to each corresponding section of the X-ray system to facilitate adjustment of the X-ray system for the selected clinical procedure.

8. The method of claim 7 wherein an edit interface restricts changes to the optimal operating parameters from their default settings to an upper and a lower limit.

* * * * *